US008297983B2

(12) United States Patent
Savitsky et al.

(10) Patent No.: US 8,297,983 B2
(45) Date of Patent: Oct. 30, 2012

(54) MULTIMODAL ULTRASOUND TRAINING SYSTEM

(75) Inventors: Eric Savitsky, Malibu, CA (US); Dan Katz, Encino, CA (US); Gabriele Nataneli, Beverly Hills, CA (US); Kresimir Petrinec, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/481,712

(22) Filed: May 25, 2012

(65) Prior Publication Data

US 2012/0237913 A1 Sep. 20, 2012

Related U.S. Application Data

(63) Continuation-in-part of application No. 13/243,758, filed on Sep. 23, 2011, which is a continuation of application No. 11/720,515, filed as application No. PCT/US2005/043155 on Nov. 30, 2005, now abandoned.

(60) Provisional application No. 60/431,488, filed on Nov. 30, 2004.

(51) Int. Cl.
*G09B 23/28* (2006.01)
*G06G 7/48* (2006.01)

(52) U.S. Cl. ............. 434/262; 703/3; 703/11; 434/322; 434/267; 600/416; 600/437; 600/441

(58) Field of Classification Search ................. 434/186, 434/219, 262, 267, 272, 322, 350; 703/1, 703/11, 3; 600/416, 437, 440, 441, 458; 382/128, 276, 283

See application file for complete search history.

(56) References Cited

U.S. PATENT DOCUMENTS

| 5,546,943 A * | 8/1996 | Gould .......................... 600/425 |
| 5,609,485 A | 3/1997 | Bergman et al. |
| 5,701,900 A | 12/1997 | Shehada et al. |
| 5,767,839 A | 6/1998 | Rosenberg |
| 5,769,640 A * | 6/1998 | Jacobus et al. ................ 434/262 |
| 5,882,206 A * | 3/1999 | Gillio ............................ 434/262 |
| 6,516,213 B1 | 2/2003 | Nevo |
| 6,896,650 B2 | 5/2005 | Tracey et al. |
| 6,916,283 B2 | 7/2005 | Tracey et al. |
| 7,037,258 B2 | 5/2006 | Chatenever et al. |
| 7,371,068 B2 | 5/2008 | Lloyd et al. |
| 7,794,388 B2 | 9/2010 | Draxinger et al. |
| 7,835,892 B2 * | 11/2010 | Butsev et al. ..................... 703/3 |
| 7,857,626 B2 | 12/2010 | Toly |
| 2002/0168618 A1 | 11/2002 | Anderson et al. |
| 2005/0181342 A1 | 8/2005 | Toly |
| 2009/0148012 A1 * | 6/2009 | Altmann et al. .............. 382/128 |
| 2010/0179428 A1 * | 7/2010 | Pedersen et al. .............. 600/443 |

* cited by examiner

*Primary Examiner* — Kang Hu
(74) *Attorney, Agent, or Firm* — Cislo & Thomas, LLP (57) ABSTRACT

An ultrasound training system having a data capture module, a digital asset management module, a validation module, didactic content, a media asset production module, an integration layer, an internet-based portal, a software client, and a peripheral probe. The combination of the disclosed elements creates a system that enables the creation and delivery of high-quality ultrasound education and training in a low-cost, widely deployable, and scalable manner, with a facilitated method for processing orders and financial transactions between customers and content providers.

13 Claims, 6 Drawing Sheets

| ID | Patient | Pathology | Anat Type | Anat Log | Point | Sonographer | Reviewer | Rating |
|---|---|---|---|---|---|---|---|---|
| 212 | P47 | | Hollow Viscous – Bladder | Abdominal Suprapubic | Point C | NM | cf<br>DK<br>TS<br>CP | (X) Not acceptable<br>(X) Not acceptable<br>( ) Acceptable<br>( ) Acceptable |
| 211 | P47 | | Hollow Viscous – Bladder | Abdominal Suprapubic | Point B | NM | cf<br>DK<br>TS<br>CP | (X) Not acceptable<br>(X) Not acceptable<br>(X) Not acceptable<br>(X) Not acceptable |
| 213 | P47 | | Hollow Viscous – Bladder | Abdominal Suprapubic | Point B | NM | cf<br>DK<br>TS<br>CP<br>sf | (X) Not acceptable<br>(X) Not acceptable<br>( ) Marginal<br>( ) Marginal<br>( ) Marginal |

MULTIMODAL ULTRASOUND TRAINING SYSTEM

CROSS-REFERENCES TO RELATED APPLICATIONS

This patent application is a continuation-in-part and claims the benefit of U.S. patent application Ser. No. 13/243,758 filed Sep. 23, 2011 for Multimodal Ultrasound Training System, which is a continuation of U.S. patent application Ser. No. 11/720,515 filed May 30, 2007 now abandoned for Multimodal Medical Procedure Training System; which is the national stage entry of PCT/US05/43155, entitled "Multimodal Medical Procedure Training System" and filed Nov. 30, 2005, which claims priority to U.S. Provisional Patent Application No. 60/631,488, entitled Multimodal Emergency Medical Procedural Training Platform and filed Nov. 30, 2004. Each of those applications is incorporated here by this reference.

This patent application also claims the benefit of U.S. Provisional Application Ser. No. 61/491,126 filed May 27, 2011 for Data Acquisition, Reconstruction, and Simulation; U.S. Provisional Application Ser. No. 61/491,131 filed May 27, 2011 for Data validator; U.S. Provisional Application Ser. No. 61/491,134 filed May 27, 2011 for Peripheral Probe with Six Degrees of Freedom Plus 1; U.S. Provisional Application Ser. No. 61/491,135 filed May 27, 2011 for Patient-Specific Advanced Ultrasound Image Reconstruction Algorithms; and U.S. Provisional Application Ser. No. 61/491,138 filed May 27, 2011 for System and Method for Improving Acquired Ultrasound-Image Review. Each of those applications is incorporated here by this reference.

TECHNICAL FIELD

This invention relates generally to systems and methods for providing medical training, and more specifically to medical training systems and methods that at least partly involve simulations of medical procedures and operations, particularly ultrasonography.

BACKGROUND ART

A paradigm shift is taking place in the world of medicine. Point-of-care ultrasonography is redefining the very essence of the physical examination and the way clinicians practice medicine. This portable, high-quality, digital imaging technology has been shown to significantly improve the quality of healthcare. It allows physicians to make more informed decisions and provide superior patient care. Coined the "stethoscope of the future," point-of-care ultrasonography can be practiced at almost any patient care site from a resource-constrained rural setting to a modem urban emergency department. Point-of-care ultrasound refers to the use of portable ultrasonography at a patient's bedside for diagnostic (e.g., symptom or sign-based examination) and therapeutic (e.g., image-guidance) purposes.

Ultrasound applications have continued to expand in the past decade. The spectrum of users now includes virtually every type of medical practitioner, ranging from nurses and primary care providers to most every physician subspecialist. There are approximately 4,000,000 potential users (nurses and physicians) in the United States and an estimated 24,000,000 globally. The principal barrier to use of this life-saving technology is lack of ultrasound training. User adoption is limited by the psychomotor skills required to manipulate an ultrasound probe coupled with the ability to interpret the resulting ultrasound images. It is clear that medical education must catch up with the expanded use of ultrasonography if tomorrow's practitioners are to provide superior healthcare for their patients.

Point-of-care ultrasonography has the potential to save hundreds of millions of dollars on an annual basis across health systems. It has the capacity to revolutionize patient care and improve procedural efficacy, decrease complications, and limit pain and suffering. A primary barrier to future universal adoption of this operator-dependent "stethoscope of the future" is the lack of widespread, efficient, and affordable training solutions. The acquisition of ultrasound skills has traditionally been limited by high opportunity costs.

Developing competence on performing ultrasonography and applying the results to clinical care is understandably a complex process. It requires integrated cognitive (image interpretation) and psychomotor (optimal image window acquisition) skills. Once an optimal image window is acquired and correctly interpreted, the information needs to be correctly applied to patient care. The opportunity cost of training healthcare providers on ultrasonography is extremely high. Optimal training requires: (1) a qualified instructor; (2) trainees; (3) an ultrasound machine; and (4) a patient with a pathologic condition. All of these elements must come together in the same place and at the same time. Furthermore, trainees must be exposed to a sufficient number of new patients exhibiting distinct pathologic conditions over an extended period of time to attain adequate mastery. It may take months to years before a care provider is able to scan a sufficient number of patients with certain pathologic conditions (e.g., leaking abdominal aortic aneurysm) to develop competence, especially considering that these clinical encounters are unpredictable. The inability to train on sufficient numbers of pathologic cases (abnormals) is a recognized impediment to ultrasound competency.

Currently available training methods all have significant limitations. These include clinical bedside teaching, attending hands-on training courses, use of phantom models, and high-fidelity yet very expensive ultrasound simulator workstations. They may involve bulky training platforms that require multiple users to visit a simulation center (e.g., UltraSim®, CAE Healthcare) or require the presence of an actual ultrasound machine (e.g., Blue PhantommI™). These ultrasound-training solutions employ high-priced dedicated computer hardware and software that does not deploy over the Internet. Alternative training products provide a limited library of purely didactic training solutions that are not accompanied with any hands-on training experience (e.g., EMSONO).

DISCLOSURE OF INVENTION

We now disclose a complete and integrated ultrasound training solution that comprises the critical components required to capture and process real-patient data at a patient's bedside, combine it with didactic content and assessment modules, and deliver it to end-users through multiple portals in a low-cost, highly efficient, and scalable manner for use on personal computers and portable computing devices. It combines the features of a fully interactive ultrasound simulator with the scalability of online learning. The key features of this described solution are: (1) a low-cost, anywhere-anytime ultrasound training solution using a laptop computer or other portable computing device; (2) flexibility to train psychomotor skills for more than one type of procedure, at a variety of skill levels, on the same platform with an expandable architecture for adding case content; (3) low cost and portability to enable wide-scale deployment into the hands of healthcare providers and beyond training programs restricted to dedicated simulation centers; (4) integration with curriculums directly adapted to the individual, based on principles of learning sciences, that teach what the trainee needs to learn and provides continuous embedded assessment and feedback; and (5) an Internet-based content delivery and financial transaction model specific to acquiring didactic education, hands-on training, and assessment of ultrasound knowledge and skill.

Accordingly, one aspect of the invention can be described as an ultrasound training system having a data capture module, a digital asset management module, a validation module, didactic content, a media asset production module, an integration layer, an internet-based portal, a software client, and a peripheral probe.

The data capture module includes software loaded on a laptop computer with a display screen. The software has computer executable instructions to provide synchronous real-time capture of ultrasound images, physiologic patient monitoring outputs, scene video, and ultrasound probe motion data at a patient's bedside. The ultrasound images are organized in a volumetric format. The software detects ultrasound probe geometry and one or more internal calibration parameters of the ultrasound probe. The software further has computer executable instructions to reconstruct an ultrasound volume and to display at least a portion of the reconstructed ultrasound volume on the display screen of the laptop computer. The data capture module also includes a tracking device to determine the ultrasound probe motion data and a video camera to capture the scene video. The corresponding ultrasound images, reconstructed ultrasound volume, physiologic patient monitoring outputs, scene video, ultrasound probe motion data, ultrasound probe geometry, and one or more internal calibration parameters of the ultrasound probe together define one case volume in a data library.

The digital asset management module includes a production data server and one or more relational databases that receive and store information from the data capture module. The digital asset management module includes computer executable instructions to enable collection, archival, retrieval, and transfer of digital assets. The digital assets include one or more of the case volumes. The digital asset management module also includes computer executable instructions to allow data versioning, data back-up, secure data transfer to the production data server, data post-processes, and data editing.

The validation module includes software having computer executable instructions to manage the upload, storage, and assessment of the case volumes. The software also provides a multi-step assessment process for the reconstructed ultrasound volume to produce a validated case volume, and the assessment process includes a questionnaire for one or more reviewers. The software further evaluates the reconstructed ultrasound volume for technical viability and educational value. The validation module further informs the one or more reviewers that content is available for review, formats the available content, and presents the formatted available content to the one or more reviewers. The formatted available content may include a video, a simulation volume, a comment field, and a visual metaphor field, where the visual metaphor field allows the reviewer to insert a visual metaphor to express an overall impression of the video and the simulation volume. A visual metaphor may be, for example, a static or animated symbol, gesture, word, or any other form of communication to convey an overall impression, judgment, feeling, comment, and the like. By way of example only, visual metaphors include, but are not limited to, smiley faces (and faces with any other expression), thumbs up/down icons, labels, and the like.

The didactic content includes a curriculum that pertains to a selected medical topic, in-module questions and answers, and end-of-module questions and answers. The media asset production module includes media elements pertaining to the didactic content, and the media elements may include medical illustrations and video segments.

The integration layer receives a validated case volume from the validation module and media elements from the media asset production module. The integration layer may include a graphical user interface, a video player, and computer executable instructions to allow navigation between the media elements and the validated case volume and to administer to a user one or more interactive quizzes. The integration layer couples the validated case volume to the media elements to produce an integrated case volume.

The interne-based portal includes an online storefront that provides user access to the integrated case volume and didactic content for navigation of the integrated case volume. The software client manages the download of the integrated case volume from the interne-based portal. The software client may also connect periodically to a remote server to retrieve information about available updates.

The peripheral probe includes a mock ultrasound probe in communication with a computing device of the user. The mock ultrasound probe includes a six degree of freedom sensor. In some embodiments, the mock ultrasound probe may further include a force detection sensor to detect compressive force on the mock ultrasound probe. The peripheral probe allows the user to navigate the downloaded integrated case volume and thereby simulate an ultrasound imaging session.

The combination of the disclosed elements creates a system that enables the creation and delivery of high-quality ultrasound education and training in a low-cost, widely deployable, and scalable manner, with a facilitated method for processing orders and financial transactions between customers and content providers. Also, a person of ordinary skill would recognize that not all of the features mentioned above are required for some versions in the disclosed system.

BEST MODE FOR CARRYING OUT THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

Figure 1:
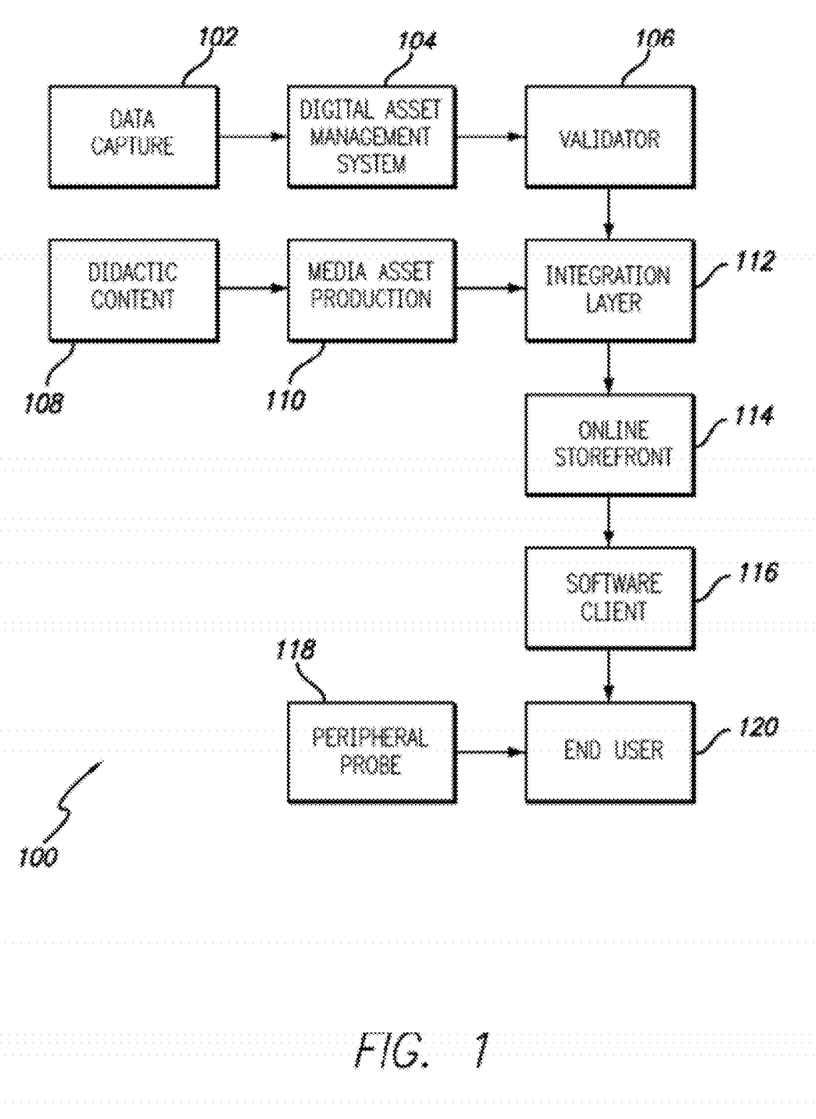
FIG. 1 is a schematic overview of the disclosed ultrasound training system.

By reference to FIG. 1, the disclosed ultrasound training system 100 preferably includes a data capture module 102, a digital asset management module 104, didactic content 108, a media asset production module 110, an integration layer 112, an internet-based portal 114, a software client 116, and a peripheral probe 118. In some embodiments, a validation module 106 may also be included in the training system 100. A detailed description of these technical elements follows.

Bedside Data Capture and Processing Using the Digital Acquisition, Reconstruction, and Simulation Interface:

The data capture module 102, or data acquisition, reconstruction, and simulation software (DARSI), allows for synchronous real-time capture of ultrasound images, physiologic patient monitoring outputs, scene video, and optionally ultrasound probe motion on a standard laptop, at the patient's bedside. Data acquired from the ultrasound machine is organized in a volumetric format that is amenable for simulation in the training software. The acquisition software works with a variety of ultrasound machines, including older models that do not provide 3D or 4D acquisition capabilities. If the ultrasound machine does not provide built-in functionality to acquire volumetric data, ultrasound images can be captured directly from the video output of the ultrasound machine and imported into a computerized system that organizes ultrasound data into a volumetric form. In some embodiments, for example, in devices that may not have 3D or 4D capabilities built in, the motion of the ultrasound probe motion can be captured using an inertial, electromagnetic, or optical tracking device with a sensing component or other tracking reference firmly attached to the probe (or embedded within it). Scene video may be captured using a single low-cost video camera, such as a commodity web-camera. In the preferred embodiment, all input sources are connected to a single laptop running the acquisition software. The software component automatically detects the geometry and internal calibration parameters of the ultrasound probe (e.g., probe type, depth setting, cropping area, volume-bounding box) and constructs an ultrasound volume (reconstructed volume) from raw data. Reconstructed volumes are immediately ready for validation, and ultrasound slices simulated from the reconstructed volume are displayed on screen. The sonographer may visually inspect captured and reconstructed data and make the decision of whether the scan needs to be repeated, for example, when motion artifacts are present or the desired pathology is not properly captured in the scan. Physiologic monitoring equipment like cardiac, respiratory, tissue deformation sensors, and plethysmography, among others, can be connected (as needed) and respective data inputs synchronized to probe motion and ultrasound data capture.

In the presently envisioned best mode, following ultrasound data collection at the patient's bedside, the data collection operator makes further edits to associated digital annotation files (annotation data) reporting detailed information about the patient, pathology and other information of clinical relevance. Annotation data is compared to notes collected on each individual patient case, which include patient history and diagnosis. Annotation data files include the following information: patient ID, anatomy type, anatomy location, chief complaint, mechanism of trauma, pathology, probe type, sonographer ID, identification of scanning point location, and the type of scan performed. Upon finalizing the annotation data, datasets are organized into folders or other types of digital archive (e.g. a single zip file with a descriptive file name) by the date of data collection and then duplicated on a server system for back up. In some embodiments, the data generated by the software includes the reconstructed ultrasound volume, patient data, case data, volume metadata, scene videos, source ultrasound videos and reconstructed ultrasound videos. Ultrasound volumes arc repositioned and aligned to correct their orientation in three-dimensional space with respect to the patient's body. This is accomplished by comparing the alignment of the ultrasound probe in the scene video with the alignment of the virtual probe in relation to the virtual body. This data comprises one case volume in a data library. Once the data is captured and reconstructed, the case volume is uploaded to the Digital Asset Management System (DAMS) 104.

Figure 2:
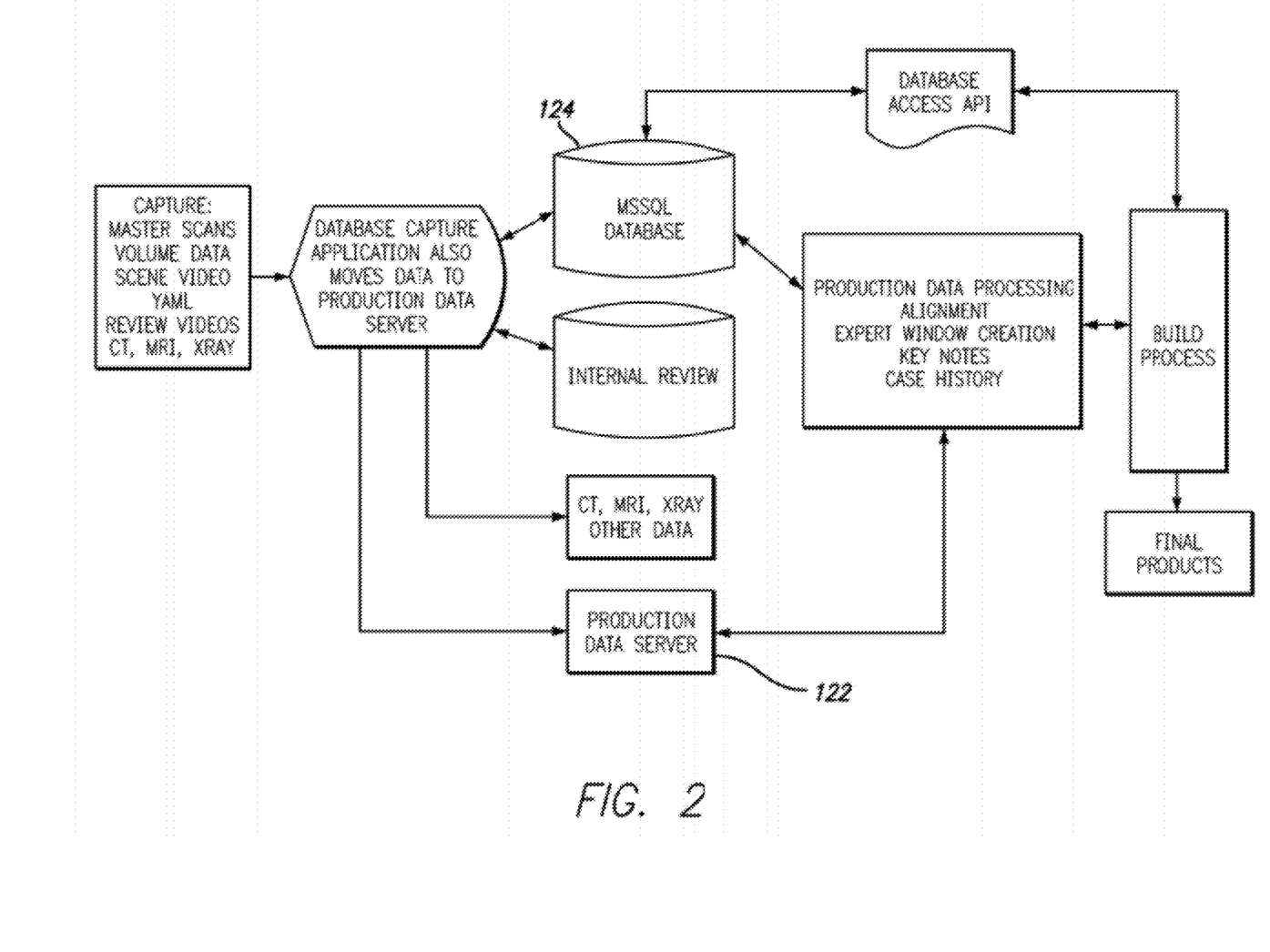
FIG. 2 is a schematic of a version of the digital asset management module in accordance with the disclosed ultrasound training system.

A Method for Organizing and Storing, Case Data Including Reconstructed Three-Dimensional Ultrasound Data and a Process for Retrieval and Transfer of Data:

The Digital Asset Management System (DAMS) 104 enables the collection, archival, retrieval, and transfer of digital assets which include case volumes, scene video, annotation data, and optionally other forms of medical imaging such as CT scans. This system stores all data in one or more relational databases 124 and provides functionality for versioning, back-up, and secure transfer of data to a production data server 122. The DAMS 104 interacts with other software components for data post-processing and editing. Relevant interactions include the alignment of case volumes, alignment of graphic user interface features, integration of didactic instructional elements and hands-on training applications. A separate build server securely retrieves assets from the DAMS 104 and compiles them along with the necessary software into digital bundles ready for delivery through the on-line storefront 114. A version of the DAMS 104 is shown in FIG. 2.

A Process for Post-Image Acquisition Expert Review, Tagging, and Organization of Case Volumes:

The validator, or validation module 106, is a technology that provides for easy prequalification and assessment of case volumes for education, training, and radiology workflow processes. In some embodiments, data generated by the data capture module 102, or DARSI, include reconstructed ultrasound datasets, patient data, case data, volume metadata, scene videos, source ultrasound videos, and master sonographer ultrasound videos. This data comprises one case volume in the data library. Once the data is captured and reconstructed, the case volume is processed by the DAMS 104 for loading into the validator 106. The validator 106 is a secure application, which manages the upload, storage, and expert assessment of ultrasound case volumes. Case volumes that are assessed positively will be submitted for inclusion in the simulation software or radiology workflow processes. The validator 106 provides a multi-step assessment process to determine the overall quality of the ultrasound reconstruction, and to evaluate specific qualities of the reconstructed volumes in terms of technical viability as well as educational value in a medical context.

To ensure proper security, user authentication preferably is required to gain access to the validator application 106. In the preferred version, technicians have access to view all data, upload new case files, and edit existing case data; reviewers have the ability to review existing cases, edit case data, and download simulation volumes; and administrators have full access to create and edit data as well as to create and manage users in the system.

Figure 3A:
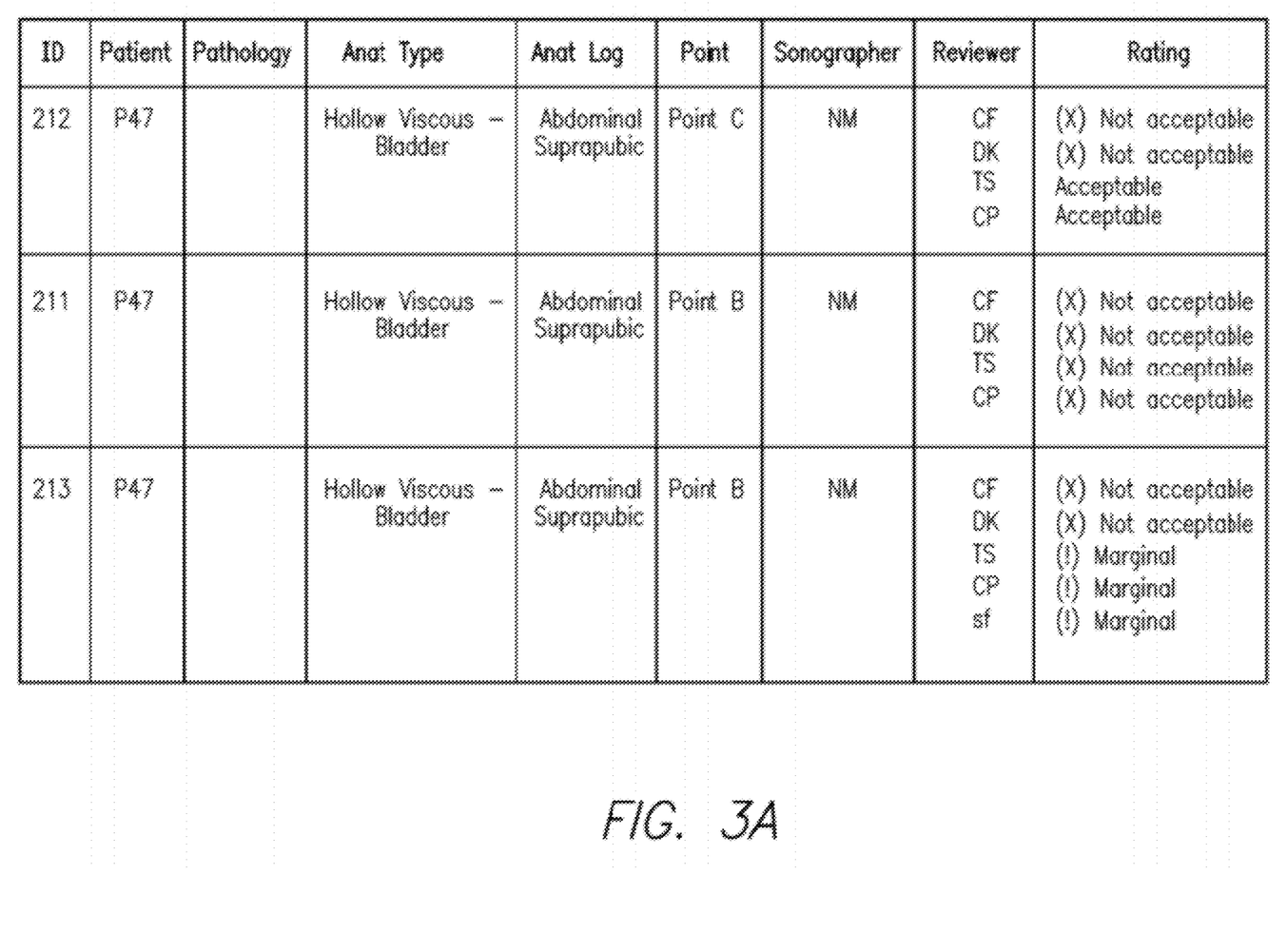
FIG. 3A is a sample of information found in a version of the validator of the disclosed ultrasound training system.

Ultrasound case volume data is uploaded by a technician via a digital form. The data is processed, validated, and entered into an internal database upon success. The technician is then routed to a new page, where the data may be edited if necessary. Once the new case is uploaded and saved, the validator 106 informs all reviewers that new content is available for review. When the reviewer logs in to the system, he or she will be presented with a list of cases that are available for review. FIG. 3A shows a sample of information that could appear on a validator page.

Figure 3B:
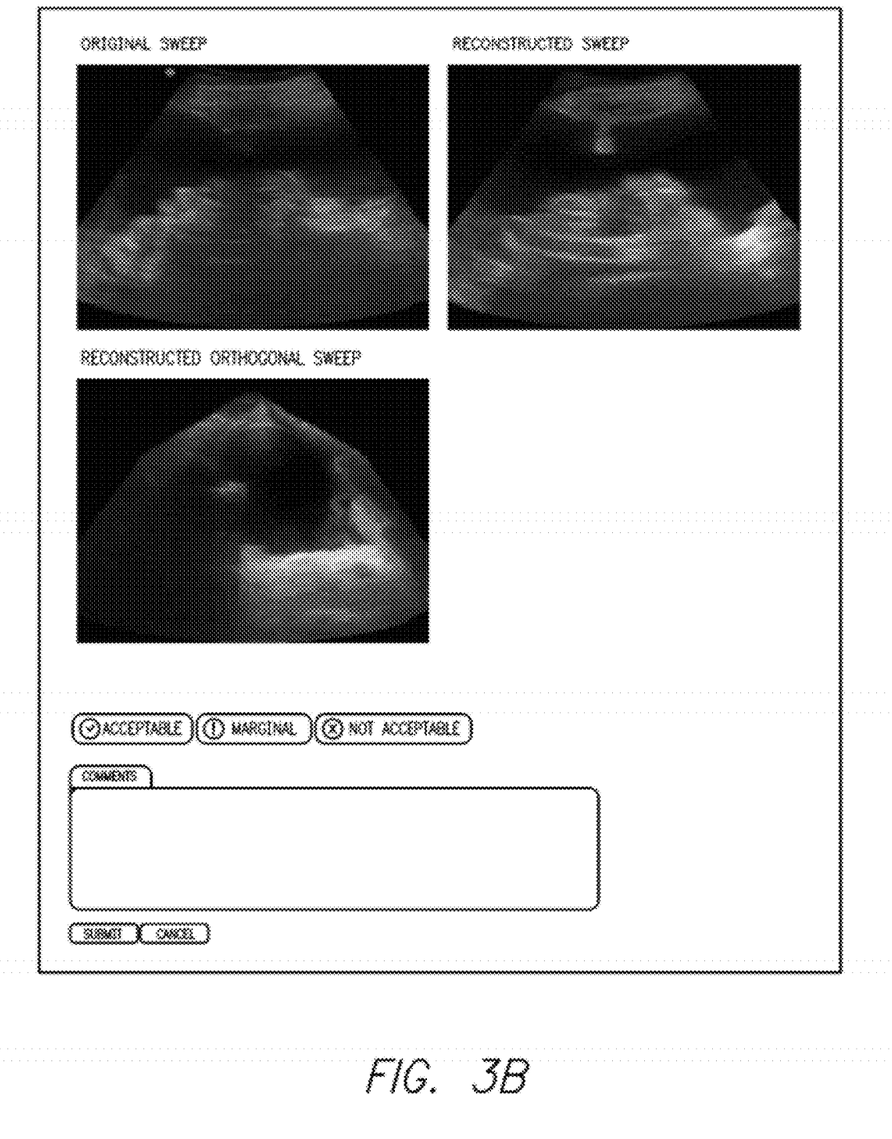
FIG. 3B is a sample of other information found in a version of the validator of the disclosed ultrasound training system.

The system additionally provides the ability to perform a detailed review. By organizing the review process over multiple tiers, it is easy to see the results of each case at a glance, get an impression of the overall quality, and find links to more detailed information if needed. The review page features videos 126, simulation volumes 128, a comment field 130, and a visual metaphor 132 to express the reviewer's overall impression as well as tools for producing a detailed review if necessary (FIG. 3B). A visual metaphor may be any static or animated symbol, gesture, word, or any other form of communication to convey an overall impression, judgment, feeling, comment, and the like of the reviewer.

To provide additional guidance, a questionnaire may be provided to help the reviewer generate an objective assessment of a case volume. While the validator 106 may not provide any direct provisions for interacting with ultrasound data, additional software, possibly external to the validator 106, may be provided to allow a more thorough investigation of a case volume with the same peripheral probe 118 to be used with the ultrasound training solution 100. Once a case volume has been validated and approved for inclusion on the product it will be submitted to the integration layer 112.

A Process for Creation of Didactic Instructional Content with Embedded Knowledge Assessment and Media Asset Integration that Directly Couples with Existing Case Volumes:

The didactic content 108 development process requires involvement of a medical subject matter expert (SME) director, medical content developers, digital media production manager, a digital media production team, and a quality assurance team. The process begins subsequent to selection of a relevant educational topic and delegation of appropriate roles and responsibilities by the medical director.

A curriculum is established specific to the selected topic and a first-draft multimedia presentation is created (e.g., PowerPoint or Keynote format). A written transcription of audio elements is provided to the medical director for primary review or distribution to an alternative subject matter expert for external review. The subject matter experts also write in-module and end-of-module questions and answers for inclusion in the final deliverable.

Medical content editing, feedback, and sign-off are performed in an iterative fashion under the direction of the medical content editor. As part of the media asset production 110, digital media elements are commissioned and signed off upon when completed and reviewed. The primary content developer creates a second-stage multimedia presentation for review and final sign-off.

Concurrent with the medical editing process the production team gains copyright clearance on all media elements included in the SME presentation, begins production on any new media elements (medical illustration, video segments, etc.,), and begins standardizing media formats for web-based delivery via upload into a Learning Content Management System (LCMS) or installed into a laptop or portable computing device.

Once the course is built in the LCMS system, and available via the web, the medical team and the course SME will walk through each individual slide reviewing for any medical or content errors. Any problems, inaccuracies, errors, bugs, and the like (issues) will be submitted to the production manager and logged in a software development log appropriately. The production team will then address each individual issue until satisfactorily resolved. The medical team and course SME will review the online course (multiple iterations of review) until all bugs have been resolved.

A technical work product quality assurance process is performed in parallel with medical content quality assurance, a technical quality assurance specialist will begin reviewing potential issues in the online course (e.g., checking functionality in multiple browsers and on multiple operating systems, playing each individual video included in the course from start to finish, etc.,).

Figure 4:
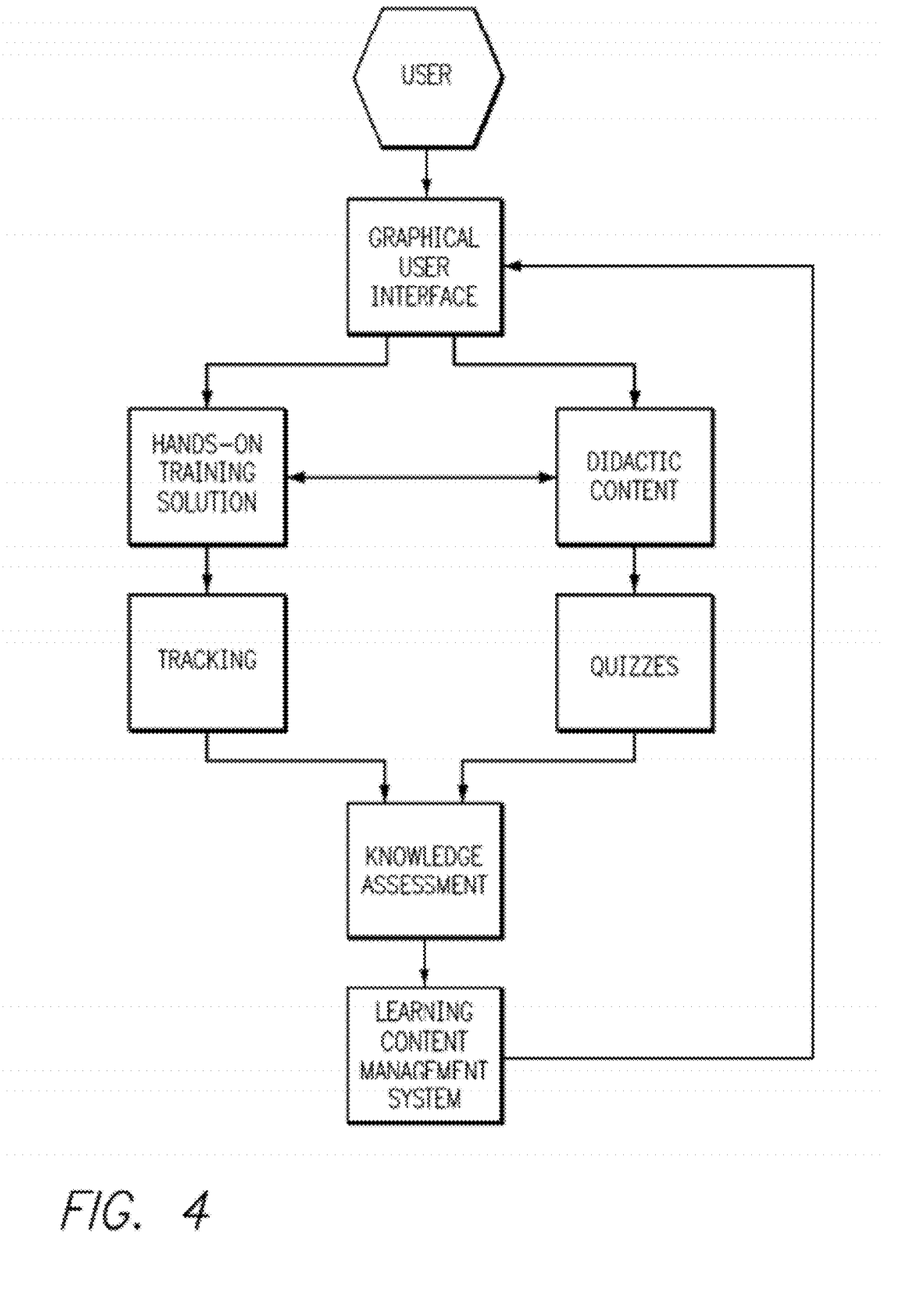
FIG. 4 is a schematic overview of a version of the integration layer of the disclosed ultrasound training system.

Method for Integration of Didactic Instruction and Hands-On Training (Case Volumes):

The integration 112 of the didactic content 108 and the case volumes into an appropriate graphic user interface linked to a mock ultrasound probe 118 coupled to a motion sensing device, as described in this invention, provides a unique ultrasound teaching and hands-on training experience. Didactic ultrasound instruction occurs in the form of text content, still imagery, or video clips with or without audio narration created by subject matter experts. Questions coupled to answers with guided feedback and automated knowledge assessment modules are also included as part of the didactic instruction 108. In the preferred embodiment, case volumes comprise real patient-based three-dimensional (3D) ultrasound data sets, rather than synthetically generated data.

The integrator 112 couples relevant didactic instruction 108 with selected case volumes for ultrasound education and training purposes. The integrator 112 consists of: (1) graphical user interface (GUI); (2) a video player that provides video/audio freeze, navigation, and playback capability; (3) the ability to navigate between didactic instruction (e.g., teaching modules) and hands-on training modes (case volumes) in a seamless manner; and (4) the ability to administer interactive quizzes (automatically scored with customized user feedback).

A user's ultrasound training experience is further augmented when dedicated didactic instruction 108 provides relevant information on subject matter that comprises case volumes or a brief tutorial specific to each case volume. The didactic instruction 108 that is linked to each respective case volume provides the trainee with: (1) navigation instructions that localize relevant findings within the case volume by an expert sonographer; (2) annotated findings within case volumes; (3) descriptions of relevant anatomy; (4) image optimization advice; and (5) assessment of a trainee's knowledge through a series of questions. Image optimization refers to the following: 1) how to position the probe to get the best view of the relevant anatomy, 2) how to change the settings of the ultrasound device to get the cleanest rendering of relevant anatomy, and 3) how to use additional features of an ultrasound device (e.g. Power Doppler) to investigate relevant the anatomy.

Linkage of an Adaptive Learning Platform Comprising Didactic Instruction, Knowledge Assessment, Hands-On Training and an Online Learning Content Management System:

To enhance the learning experience provided to the user 120, the described system has provisions for tracking the performance of the trainee and adapting the content to his or her specific learning needs. This is referred to as an adaptive learning platform. The performance of the user 120 is tracked by either gathering raw data about the usage of the hands-on training component or through regular evaluations of content knowledge in the form of short quizzes. The adaptive learning platform uses a rule-based or statistical approach (or both) to quantify the mastery of the material achieved by the user 120 and instruct the Learning Content Management System (LCMS) to present the user 120 with new content appropriate to his or her level of understanding and performance.

An Internet-Based Portal for Content Ordering and Delivery:

The described internet-based portal 114, or online store, provides access to integrated didactic instruction, knowledge assessment, and hands-on training modules. Internet users can purchase a personalized selection of didactic instruction and hands-on training content, as well as the software technology necessary for its navigation through the internet-based portal 114. (FIG. 5) Training materials are organized in independent modules, which include hands-on training case volumes and linked didactic instruction. Each training module may be purchased separately, or as part of a collection tailored to a specific user (e.g., an individual nurse) or user group (e.g., cardiologists) preference. The training modules are stored in a secure remote storage server and accessible through an online storefront. When the user purchases content from the online store 114 he or she will receive a software client 116 that manages the download of the purchased training modules and related software and enforces proper use of the content by means of a digital rights managements (DRM) system.

Alternatively the client 116 may provide the content directly to the user 120 without prior download of the entire data set using a streaming solution. The client 116 provides access to the knowledge assessment system and LCMS either through local integrated components or a remote server-based solution. The infrastructure required to support upload and download of large amounts of content to users utilizes either a traditional client-server model, a peer-to-peer model, or a hybrid model of content delivery.

Figure 5:
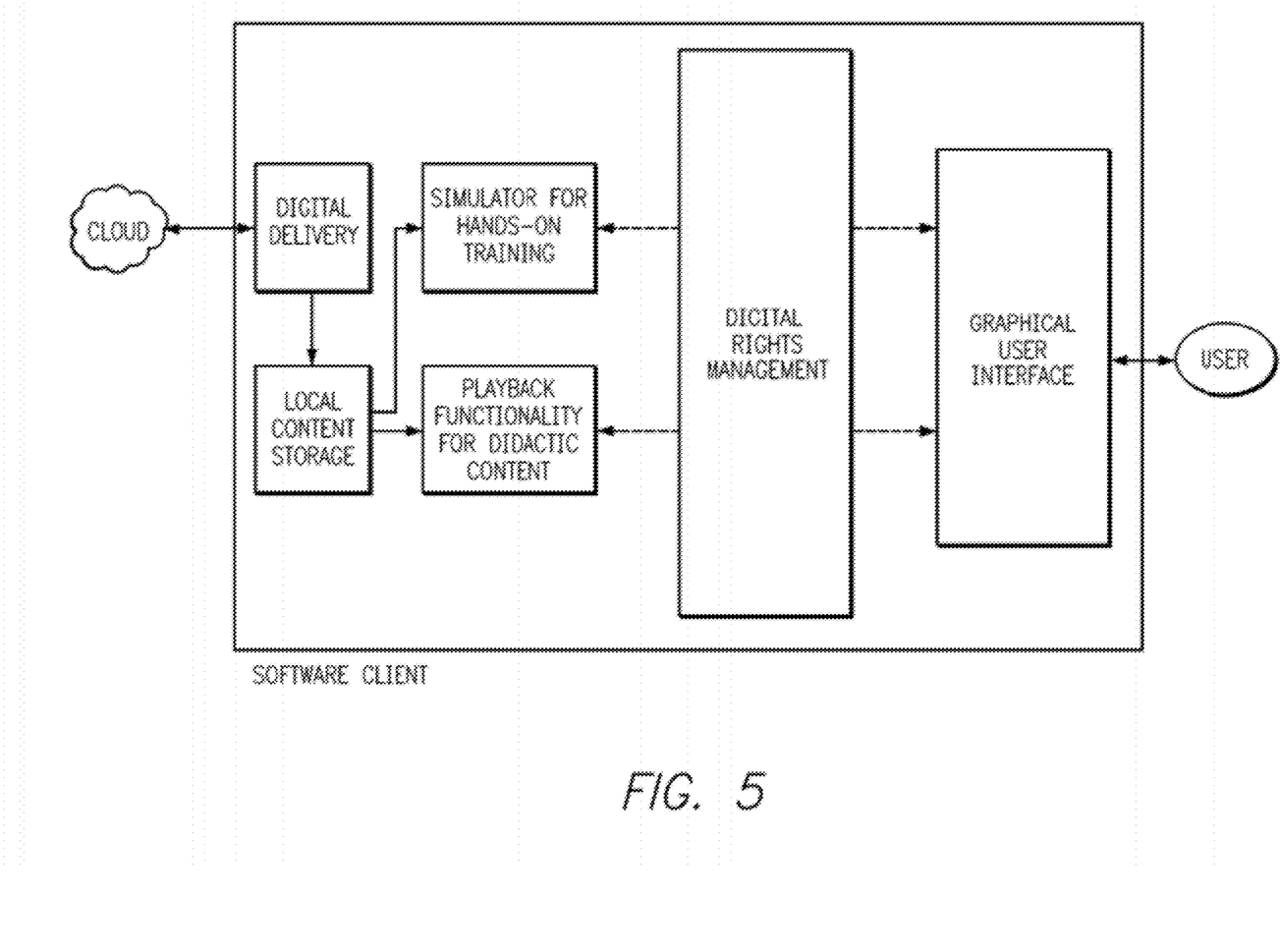
FIG. 5 is a schematic of a version of the internet-based portal of the disclosed ultrasound training system.

A Process of Online Customer Ordering and Online Financial Interaction Processing:

Online users place orders through the internet-based portal 114 and a linked online financial interaction application processes the order and accordingly credits the financial accounts of the operator of the disclosed system. The online storefront 114 provides users with the basic capabilities found in modern e-commerce systems. These features include: (1) the ability to browse an extensive online catalog; (2) the ability to process purchases and transactions securely; (3) the ability to create user accounts and define customized profiles; and (4) the ability to download content digitally. The modem e-commerce system appropriately credits and transfers monies to accounts of the operator of the disclosed system based on previously agreed upon financial arrangements.

A Method of Delivery and Integration of a Portable, Peripheral Mock Ultrasound Probe and Alternative Plug-In Medical Devices to a Subscriber's Personal Computer or Portable Computing Device:

The mock ultrasound probe 118 will be delivered to users based on specifications agreed upon during the customer and internet-based portal transaction (e.g., business class mail). The mock ultrasound probe 118 is designed to plug into the user's personal computer or portable computing device. In alternative embodiments, a wireless communication mode of data transfer may be utilized instead of a wired serial data connection. Alternative plug-in medical devices include mock handheld needles, instruments (e.g., endoscope), or mock anatomic physical recreations (e.g., torso mannequin). Additionally, the mock ultrasound probe 118 may provide expansion ports for connecting add-on components for extending the hardware capabilities of the device (e.g., provisions for endocavitary simulations).

A Process for Updating (Upload and Download of Information) A User's Ultrasound Training Solution Using a Client-Server Mode Of Interaction (E.G Product Software Updates):

The software client 116, similarly to other established clients for digital delivery, preferably has the ability to regularly connect to a remote server and retrieve information about available updates. Updates will come in several forms, including: (1) updates of the client; (2) updates of the simulation and playback software; and (3) updates of the training modules. Each update will deliver progressive improvements.

Integration of a Mock Ultrasound Probe (6+1 DOF Sensor) that is Customized to Enable the Key Features Used by Clinicians During the Performance of Bedside Ultrasonography (E G., Compression Sensing):

Current state of the art (i.e., off the shelf technology) includes 3- and 6-degrees of freedom (DOF) motion sensors. The first kind is restricted to measuring orientation along three distinct orthogonal axes, while the second kind augments orientation with three measurements of displacement along each of the component axes for a total of six degrees of freedom. The sensor 118 utilized with the disclosed system provides one further degree of freedom for measuring compression by means of an additional sensing component. We refer to this configuration as a 6+1 DOF sensor 118. The primary purpose of this device is to provide adequate control for software applications, especially in the field of ultrasound simulation, where the added mode of sensing is necessary to emulate real tasks faithfully in a simulated ultrasound-imaging environment. The device is built in such a manner that it may be encased in various types of enclosures that mimic the shape and tactile feel of other devices to be simulated in software.

The 6+1 DOF motion sensor 118 is a motion-sensing peripheral device that interfaces with a personal computer's input channel, such as universal serial bus (USB), Firewire, Thunderbolt, or other contact-less port. Similar to a handheld motion-controller wand, sensor components within the sensor 118 track the device's position and orientation in three-dimensional space. Various embodiments of these sensor components may include inertial, magnetic and/or optical sensors.

While the present invention has Veen described with regards to particular embodiments, it is recognized that additional variations of the present invention may be devised without departing from the inventive concept.

INDUSTRIAL APPLICABILITY

This invention may be industrially applied to the development, manufacture, and use of medical training systems, particularly those that involve ultrasonography.

What is claimed is:

1. An ultrasound training system, the system comprising:
(a) a data capture module, the data capture module comprising software loaded on a laptop computer having a display screen, the software having computer executable instructions to provide synchronous real-time capture of ultrasound images, physiologic patient monitoring outputs, scene video, and ultrasound probe motion data at a patient's bedside, the ultrasound images being organized in a volumetric format, the software detecting an ultrasound probe geometry and one or more internal calibration parameters of the ultrasound probe, the software further having computer executable instructions to reconstruct an ultrasound volume and to display at least a portion of the reconstructed ultrasound volume on the display screen of the laptop computer, the data capture module further comprising a tracking device to determine the ultrasound probe motion data and a video camera to capture the scene video, where the corresponding ultrasound images, reconstructed ultrasound volume, physiologic patient monitoring outputs, scene video, ultrasound probe motion data, ultrasound probe geometry, and one or more internal calibration parameters of the ultrasound probe together define one case volume in a data library;

(b) a digital asset management module, the digital asset management module comprising a production data server and one or more relational databases receiving and storing information from the data capture module, the digital asset management module including computer executable instructions to enable collection, archival, retrieval, and transfer of digital assets, the digital assets comprising one or more of the case volumes, the digital asset management module also including computer executable instructions to allow data versioning, data back-up, secure data transfer to the production data server, data post-processing, and data editing;

(c) a validation module; the validation module comprising software having computer executable instructions to manage the upload, storage, and assessment of the case volumes, the software also providing a multi-step assessment process for the reconstructed ultrasound volume to produce a validated case volume, the assessment process including a questionnaire for one or more reviewers, the software further evaluating the reconstructed ultrasound volume for technical viability and educational value, the validation module further informing the one or more reviewers that content is available for review, formatting the available content, and presenting the formatted available content to the one or more reviewers, the formatted available content comprising a video, a simulation volume, a comment field, and a visual metaphor field, the visual metaphor field allowing the reviewer to express an overall impression of the video and the simulation volume;

(d) didactic content, the didactic content comprising a curriculum pertaining to a selected medical topic, in-module questions and answers, and end-of-module questions and answers;

(e) a media asset production module, the media asset production module comprising media elements pertaining to the didactic content, the media elements including medical illustrations and video segments;

(f) an integration layer, the integration layer receiving a validated case volume from the validation module and media elements from the media asset production module, the integration layer comprising a graphical user interface, a video player, and computer executable instructions to allow navigation between the media elements and the validated case volume and to administer to a user one or more interactive quizzes, the integration layer coupling the validated case volume to the media elements to produce an integrated case volume;

(g) an internet-based portal, the internet-based portal comprising an online storefront providing user access to the integrated case volume and software technology for navigation of the integrated case volume;

(h) a software client, the software client managing the download of the integrated case volume from the internet-based portal, the software client connecting periodically to a remote server to retrieve information about available updates; and (i) a peripheral probe, the peripheral probe comprising a mock ultrasound probe in communication with a computing device of the user, the mock ultrasound probe including a six degree of freedom sensor and a force detection sensor detecting compressive force on the mock ultrasound probe, the peripheral probe allowing the user to navigate the downloaded integrated case volume and thereby simulate an ultrasound imaging session.

2. An ultrasound training system, the system comprising:
(a) a data capture module, the data capture module comprising software loaded on a computer having a display screen, the software having computer executable instructions to provide synchronous real-time capture of ultrasound images at a patient's bedside, the ultrasound images being organized in a volumetric format, the software further having computer executable instructions to reconstruct an ultrasound volume and to display at least a portion of the reconstructed ultrasound volume on the display screen of the computer, where the corresponding ultrasound images, reconstructed ultrasound volume, physiologic patient monitoring outputs, scene video, ultrasound probe motion data, ultrasound probe geometry, and one or more internal calibration parameters of the ultrasound probe together define one case volume in a data library;

(b) a digital asset management module, the digital asset management module comprising one or more relational databases receiving and storing information from the data capture module, the digital asset management module including computer executable instructions to enable collection, archival, retrieval, and transfer of digital assets, the digital assets comprising one or more of the case volumes;

(c) a validation module, the validation module comprising software having computer executable instructions to manage the upload, storage, and assessment of the case volumes, the software also providing a multi-step assessment process for the reconstructed ultrasound volume to produce a validated case volume, the assessment process including a questionnaire for one or more reviewers, the validation module further informing the one or more reviewers that content is available for review, formatting the available content, and presenting the formatted available content to the one or more reviewers;

(d) didactic content, the didactic content comprising a curriculum pertaining to a selected medical topic, in-module questions and answers, and end-of-module questions and answers;

(e) a media asset production module, the media asset production module comprising media elements pertaining to the didactic content;

(f) an integration layer, the integration layer receiving a validated case volume from the validation module and media elements from the media asset production module, the integration layer comprising a graphical user interface and computer executable instructions to allow navigation between the media elements and the validated case volume and to administer to a user one or more interactive quizzes, the integration layer coupling the validated case volume to the media elements to produce an integrated case volume;

(g) an internet-based portal, the internet-based portal comprising an online storefront providing user access to the integrated case volume and software technology for navigation of the integrated case volume;

(h) a software client, the software client managing the download of the integrated case volume from the internet-based portal; and (i) a peripheral probe, the peripheral probe comprising a mock ultrasound probe in communication with a computing device of the user, the mock ultrasound probe including a six degree of freedom sensor and a force detection sensor detecting compressive force on the mock ultrasound probe, the peripheral probe allowing the user to navigate the downloaded integrated case volume and thereby simulate an ultrasound imaging session.

3. The ultrasound training system of claim 2, where the software of the data capture module has computer executable instructions to also provide physiologic patient monitoring outputs, scene video, and ultrasound probe motion data, where the corresponding ultrasound images, reconstructed ultrasound volume, physiologic patient monitoring outputs, scene video, and ultrasound probe motion data together define one case volume in a data library.

4. The ultrasound training system of claim 3, where the data capture module further comprises a tracking device to determine the ultrasound probe motion data and a video camera to capture the scene video.

5. The ultrasound training system of claim 2, where the software of the data capture module also detects an ultrasound probe geometry and one or more internal calibration parameters of the ultrasound probe, where the corresponding ultrasound images, reconstructed ultrasound volume, ultrasound probe geometry, and one or more internal calibration parameters of the ultrasound probe together define one case volume in a data library.

6. The ultrasound training system of claim 2, where the digital asset management module also includes computer executable instructions to allow data versioning, data backup, data post-processing, and data editing.

7. The ultrasound training system of claim 2, where the digital asset management module further comprises a production data server.

8. The ultrasound training system of claim 7, where the digital asset management module also includes computer executable instructions to allow secure data transfer to the production data server.

9. The ultrasound training system of claim 2, where the software of the validation module further evaluates the reconstructed ultrasound volume for technical viability and educational value.

10. The ultrasound training system of claim 2, where the formatted available content of the validation module comprises a video, a simulation volume, a comment field, and a visual metaphor field, the visual metaphor field allowing the reviewer to express an overall impression of the video and the simulation volume.

11. The ultrasound training system of claim 2, where the media elements of the media asset production module include medical illustrations and video segments.

12. The ultrasound training system of claim 2, where the integration layer further comprises a video player.

13. The ultrasound training system of claim 2, where the software client connects periodically to a remote server to retrieve information about available updates.

* * * * *